United States Patent [19]
Webster et al.

[11] Patent Number: 5,227,528
[45] Date of Patent: Jul. 13, 1993

[54] DECOLORIZATION OF POLYALKYLENE POLYAMINES

[75] Inventors: Stephen J. Webster, Angleton; John H. Mitchell, Lake Jackson, both of Tex.

[73] Assignee: The Dow Chemical Company, Midland, Mich.

[21] Appl. No.: 876,638

[22] Filed: Apr. 30, 1992

[51] Int. Cl.⁵ .......................................... C07C 209/84
[52] U.S. Cl. ........................ 564/498; 544/358; 544/402; 564/511; 564/512
[58] Field of Search ............... 564/498, 511, 512; 544/358, 402

[56] References Cited

U.S. PATENT DOCUMENTS

| | | | |
|---|---|---|---|
| 3,428,684 | 2/1969 | Tindall et al. | 564/497 |
| 3,595,921 | 7/1971 | Pitts et al. | 564/498 |
| 3,723,529 | 3/1973 | Pitts et al. | 564/498 |
| 3,891,708 | 6/1975 | Woodrum et al. | 564/497 |
| 4,584,405 | 4/1986 | Vanderpool | 564/498 |
| 4,670,232 | 6/1987 | Crandall et al. | 423/206 R |
| 4,737,243 | 4/1988 | Simi et al. | 203/29 |
| 4,766,247 | 8/1988 | Ford et al. | 564/498 |

OTHER PUBLICATIONS

Derwent Abstract 44242S (GB 1,238,351) Imperial Chemical Inds. Ltd. (1971) Hexamethylenediamine Purifn Using Mixture of Caustic Soda and Potash.
Derwent Abstract 71148U (Japanese 4852708) Seitetsu Kagaku Co. Ltd. (1973) Decolourisation of Amines.
Derwent Abstract 90-133416/18 (EP-365850A) Tosoh Corp. (1990).

*Primary Examiner*—Richard L. Raymond
*Assistant Examiner*—Scott C. Rand
*Attorney, Agent, or Firm*—Robert M. O'Keefe

[57] ABSTRACT

A process for decolorizing polyalkylene polyamines, which comprises contacting one or more polyalkylene polyamines having an average molecular weight of greater than about 200 and less than about 1000 with carbon at a temperature greater than or equal to about 100° C. and less than or equal to about 300° C. under conditions effective to reduce the color rating of the one or more polyalkylene polyamines.

9 Claims, No Drawings

DECOLORIZATION OF POLYALKYLENE POLYAMINES

BACKGROUND OF THE INVENTION

This invention relates to processes for decolorizing polyalkylene polyamines.

Polyalkylene polyamines are well known commercial compounds having a variety of uses. The end use of these compounds influences the amount of color which is desirable in the product to be sold. Methods to purify and thereby reduce color of polyalkylene polyamines is thus very important for both a producer and an end user.

U.S. Pat. No. 3,723,529 to Pitts et al., dated Mar. 27, 1973, sets forth such a method. The disclosed process entails passing polyethylene polyamines through a carbon bed and then distilling the effluent. Pitts et al. explain that treatment with only carbon failed to decolorize the polyamines at temperatures of at least 190° C. and, in fact, led to more highly colored products in some cases. Since distillation processes are energy intensive, however, a process which facilitates removal of color in polyalkylene polyamines without such a step is highly desirable.

SUMMARY OF INVENTION

This invention, in one respect, is a process for decolorizing polyalkylene polyamines, which comprises contacting one or more polyalkylene polyamines having an average molecular weight of greater than about 200 and less than about 1000 with carbon at a temperature greater than or equal to about 100° C. and less than or equal to about 300° C. under conditions effective to reduce the color rating of the one or more polyalkylene polyamines.

DETAILED DESCRIPTION OF THE INVENTION

The one or more polyalkylene polyamines that can be decolorized according to the process of the present invention are well-known compounds. For the purposes of the present invention, it is preferred to employ a polyalkylene polyamine having or a mixture of two or more polyalkylene polyamines having an average molecular weight of greater than about 200, preferably greater than about 225, more preferably greater than about 250; less than about 1,000, preferably less than about 800, more preferably less than about 300. Suitable polyalkylene polyamines can be linear, branched, cyclic, and combinations thereof. Examples of suitable polyalkylene polyamines include
ethylenediamine, triethylenetetramine,
tetraethylenepentamine, pentaethylenehexamine,
hexaethyleneheptamine, heptaethyleneoctamine,
piperazine, aminoethylpiperazine, propylenediamine,
butylenediamine, pentamethylenediamine,
hexamethylenediamine, diethylenetriamine,
dipropylenetriamine, dibutylenetriamine,
bis(pentamethylene)triamine, bis(hexamethylene)triamine,
tripropylenetetramine, tris(hexamethylene)tetramine,
tetrapropylenepentamine, tetrabutylenepentamine,
tetrakis(pentamethylene)pentamine,
tetrakis(hexamethylene)pentamine,
pentapropylenehexamine, pentabutylenehexamine,
pentakis(pentamethylene)hexamine,
pentakis(hexamethylene)hexamine,
bis(aminopropyl)ethylenediamine,
bis(aminopropyl)diethylenetriamine, and
tris(aminopropyl)ethylenediamine. The preferred polyalkylene polyamines generally have the formula:

wherein n can be from zero to about 6 and is preferably zero, m can be from 1 to 10 and is preferably from 4 to 10, and p can be from 1 to 3 and is preferably 1, with the proviso that n and m can vary independently within a molecule from one repeating unit to the next. When a mixture of polyalkylene polyamines is treated in accordance with this invention, the examples of preferred polyalkylene polyamines include triethylenetetraamine, tetraethylenepentamine, pentaethylenehexamine, hexaethyleneheptamine, and heptaethyleneoctamine. More preferably, when a mixture of polyalkylene polyamines is treated in accordance with this invention, the polyalkylene polyamines include tetraethylenepentamine, pentaethylenehexamine, hexaethyleneheptamine, and heptaethyleneoctamine.

The one or more polyalkylene polyamines to be decolorized by the process of this invention can have a wide range of color prior to treatment. The amount of color (the color rating) of the one or more polyalkylene polyamines can be readily ascertained and depicted by using the 1953 series Gardner Color Scale. Typically, the color rating of the polyalkylene polyamines is greater than about 4 on the Gardner Color Scale, although less colored polyalkylene polyamines can be treated. More typically, the one or more polyalkylene polyamines has a color rating on the Gardner Color Scale of greater than about 6. The color rating can be higher than 13; however, the one or more polyalkylene polyamines generally has a color rating on the Gardner Color Scale less than about 15, preferably less than or equal to about 13. The amount of color removed by this process varies widely depending on several variables such as the amount and color rating of the polyalkylene polyamines to be treated: the amount, size, and condition of the carbon: and temperature. At room temperature, very little color is removed. As temperature increases, the extent of decolorization also increases reaching a maximum in the range from zero to 10 color units on the Gardner Color Scale. Above a temperature of about 300° C., the process efficacy begins to drop. The color rating of the feed to be treated decreases after treatment with this process by at least about 1, preferably at least about 4. The color rating can be reduced by this process to a value less than about 8, preferably less than about 7, more preferably less than about 5.

The carbon useful in this process can be any conventional carbon used as an absorbent. Activated carbon is preferred. Carbon and activated carbon are widely available commercially. Carbon can be rendered active using conventional procedures such as treatment with dilute aqueous hydrogen chloride. Suitable carbon can be used from a wide variety of sources. For example, carbon known as bituminous coal type and coconut shell type are well known in the art. The shape of the carbon is not critical and can be in the form of any conventional shape such as powder, granular, pellet, or the like. The surface are of the carbon can vary widely from about 500 to 1200 m²/g. Surface area is not critical to the invention. The average size of carbon used in this invention can vary widely, but finely powdered carbons are less desirable since they are difficult to separate from the polyalkylene polyamines and tend to cause plugging in a conventional continuous flow system. Any size carbon can be used which is capable of being supported in a bed without plugging, as is apparent to a skilled artisan. Generally, the carbon has a mesh size of greater than about 6 and less than about 40. Ranges of sizes may be employed such as carbons having mesh sizes of 12×40, 6×16, and 8×30. By this is meant, for example, that an 8×30 mesh carbon is small enough to pass through a size 8 mesh screen, but which does not pass through a size 30 mesh screen. A preferred size of carbon is one having what is known in the art as an 8×30 mesh size. A particularly preferred carbon within the preferred size range is a bituminous coal type carbon having a surface area of 950 m$^2$/g. An example of this preferred catalyst is Calgon TM SGL 8×30 which is commercially available from Calgon Carbon Corporation.

The process can be run either batchwise or in a continuous manner.

In a batch mode, the one or more polyalkylene polyamines are contacted with the active carbon in a closed vessel for a time sufficient to remove at least a portion of the color therein. The process of this invention can be conducted in any batch system suitably designed for such purpose as is apparent to a skilled artisan. Time will vary depending on factors such as temperature, pressure, volume of polyalkylene polyamine to be treated, and the amount of polyalkylene polyamine relative to carbon. Typically, time is greater than 0.1 hour. Preferably, time is greater than 0.5 hour. Typically, time is less than 24 hours. Preferably, time is less than 18 hours, more preferably less than 8 hours. In batch mode, the amount of carbon is at least one percent by weight relative to polyalkylene polyamine. The amount of carbon is preferably greater than about 5 percent. The batch can be stirred. Pressure can be atmospheric, sub-atmospheric, or super-atmospheric. A pad of an inert gas such as nitrogen can be maintained over the batch. After decolorization, the one or more polyalkylene polyamines can be separated from carbon using conventional techniques such as filtration.

In a continuous process, the one or more polyalkylene polyamines to be treated is contacted with one or more fixed beds of carbon. Conventional treatment apparatus are useful for this purpose. The contact time varies depending on conditions and may be expressed in terms of flow rate over carbon. Typically, the flow rate is greater than about 0.1 ml polyalkylene polyamine per 1 gram carbon per hour, preferably greater than about 0.5 ml per gram carbon per hour. The flow rate is usually less than about 5 ml per gram carbon per hour, preferably less than about 2 ml per gram carbon per hour. Pressures are preferably sufficient to maintain liquid conditions. In continuous operation, the apparatus is usually equipped in a conventional manner so that effluent is free of carbon particles.

In any mode by which the process of this invention is conducted, temperature is typically greater than or equal to about 100° C. Preferably, temperature is greater or equal to than about 150° C., more preferably greater than or equal to about 175° C. Temperature is typically less than or equal to about 300° C., preferably less than or equal to about 275° C., more preferably less than or equal to about 260° C., and even more preferably less than or equal to about 250° C. Due to the effective balance of color removal and sufficiently low rate of cracking, the most preferred temperature is about 200° C.

The activity of the carbon declines over time as color bodies become adsorbed. Therefore, the carbon will require regeneration as necessary as determined by routine experimentation and observation. Conventional procedures can be employed for this purpose. Typically, a polar solvent is used to flush the carbon and thereby remove adsorbed color bodies. It has been found that water condensate or hot water works well for this purpose, followed by drying of the carbon. The water condensate or hot water can contain dilute acid such as dilute hydrochloric acid, phosphoric acid, ammonium hydroxide or can contain bases such as sodium hydroxide and sodium borohydride. If an acid or base is present in the water condensate or hot water, hydrochloric acid is preferred.

The following examples are given to illustrate the invention and should not be interpreted as limiting it in any way. Unless stated otherwise, all parts and percentages are given by weight.

EXAMPLE 1

A one inch inside diameter stainless steel column is packed with 90 cc of carbon (Calgon TM CAL 12×40 mesh). After flushing with water to remove carbon fines, the carbon is dried with nitrogen. Temperature and pressure are maintained using conventional apparatus. A polyalkylene polyamine feed is next flowed through the carbon bed. The feed is a typical bottoms feed from a commercial reactor for the preparation of polyethylene polyamines having an average molecular weight of from 250 to 300. The feed contains about one percent triethylenetetramine, about 11 percent tetraethylenepentamine, about 43 percent pentaethylenehexamine, about 25 percent hexaethylene-heptamine, and about 20 percent heptaethyleneoctamine and higher homologs. The feed has a color rating of 13 on the Gardner scale. The flow is maintained at 1.5 ml/minute. Pressure is atmospheric. Temperature is varied from 100° C. to 250° C. At 100° C. the effluent is a Gardner 10.5. At 150° C. the effluent is a Gardner 9.5. At 200° C. the effluent is a Gardner 7. At 250° C. the effluent is a Gardner 5. In each case, the temperature is allowed to stabilize for 4 hours prior to sampling.

EXAMPLE 2

The procedure of Example 1 is repeated at 200° C. using three carbons: a 6×16 mesh coconut shell type carbon having a surface area of 1200 m$^2$/g (Calgon TM PCB 8×30 mesh): an 8×30 mesh bituminous coal type carbon having a surface area of 950 m$^2$/g (Calgon TM SGL 8×30 mesh): and a 6×16 mesh bituminous coal type carbon having a surface area of 1100 m$^2$/g (Calgon TM BPL 6×16 mesh). All three carbons are found to remove color from the polyalkylene polyamine mixture in a manner similar to that shown above in Example 1 and the 8×30 mesh bituminous coal type carbon having a surface area of 950 m$^2$/g (Calgon TM SGL 8×30 mesh) is found to remove the color at the fastest rate.

What is claimed is:

1. A one-step process for decolorizing polyalkylene polyamines, which consists essentially of contacting one or more polyalkylene polyamines having an average molecular weight of greater than about 200 and less than about 1000 with carbon at a temperature greater than or equal to about 100° C. and less than or equal to about 300° C. under conditions effective to reduce the color rating of the one or more polyalkylene polyamines.

2. The process of claim 1 wherein the polyalkylene polyamine or the mixture of two or more polyalkylene polyamines have an average molecular weight of from about 225 to about 300.

3. The process of claim 1 wherein the temperature is greater than or equal to 175° C. and less than or equal to about 250° C.

4. The process of claim 1 wherein the process is carried out as in a continuous manner wherein the flow rate is greater than about 0.5 ml and less than about 2 ml polyalkylene polyamine per gram carbon per hour.

5. The process of claim 4 wherein two or more carbon beds are employed.

6. The process of claim 1 wherein the color rating of the one or more polyalkylene polyamines is reduced to a value less than about 5 on the Gardner Color Scale.

7. The process of claim 1 wherein the carbon has an average size of from about size 4 mesh to about size 40 mesh.

8. The process of claim 1 wherein the color rating on the Gardner Color Scale of the one or more polyalkylene polyamines is greater than about 6.

9. The process of claim 3 wherein the carbon is bituminous coal type carbon having an average size of from about size 6 mesh to about size 30 mesh.

* * * * *